United States Patent [19]

Odelhög

[11] 4,385,632

[45] May 31, 1983

[54] GERMICIDAL ABSORBENT BODY

[75] Inventor: Sven O. Odelhög, Vreta Kloster, Sweden

[73] Assignee: Landstingens Inköpscentral, Solna, Sweden

[21] Appl. No.: 302,082

[22] Filed: Sep. 14, 1981

[30] Foreign Application Priority Data

Sep. 17, 1980 [SE] Sweden ............................. 8006516

[51] Int. Cl.³ ...................... A61F 13/16; A61K 49/04; B32B 23/08
[52] U.S. Cl. ................................. 604/360; 428/342; 428/514; 428/689; 428/905; 424/76; 422/5; 604/375
[58] Field of Search ............... 428/342, 514, 689, 905; 424/76; 422/5; 128/284

[56] References Cited

U.S. PATENT DOCUMENTS

| 2,762,822 | 9/1956 | Vagemus | 424/76 |
|---|---|---|---|
| 2,856,330 | 10/1958 | Vagemus | 424/76 |
| 3,172,817 | 3/1965 | Leupold et al. | 424/76 |
| 3,567,118 | 3/1971 | Shepherd | 428/905 |

FOREIGN PATENT DOCUMENTS

| 631086 | 6/1936 | Fed. Rep. of Germany. |
|---|---|---|
| 793049 | 1/1936 | France. |
| 2135321 | 12/1972 | France. |
| 80837 | 10/1952 | Norway. |
| 172480 | 8/1960 | Sweden. |
| 213959 | 7/1967 | Sweden. |
| 7804195-1 | 11/1979 | Sweden. |

OTHER PUBLICATIONS

Merck Index 9 Ed. Nos. 2636, 2640 and 2657.

*Primary Examiner*—P. Ives
*Attorney, Agent, or Firm*—Cushman, Darby & Cushman

[57] ABSTRACT

An absorbent body for collecting blood, faeces and urine contains a water-soluble copper salt which impedes bacterial growth, prevents the breaking-down of urea into ammonia and complex-binds ammonia so as to prevent the occurrence of unpleasant odor. Preferably copper acetate is used, in which even the acetate ion has germicidal effect.

2 Claims, No Drawings

GERMICIDAL ABSORBENT BODY

The invention relates to absorbent body with odor-inhibiting effect, especially a diaper, napkin or towel for collecting urine, faeces or blood.

It is known that the skin in the perineum (the region between the anus and the external sexual organs) of a human is always the home of a large number of bacteria of different type, even if strict hygiene is observed. Tests have shown that, with small individual variations, the bacteria consist to 80% of the four groups Proteus, Clebsiella, Pseudomonas and Coli. Of these, various strains of Proteus account for approximately half of the total number of bacteria.

In a healthy, adult human, these bacteria cause no real damage as long as they are only on the skin which is healthy and undamaged. When there is heavy perspiration in the perineal region, the conditions for growth of bacteria become extremely favourable, and products formed by their metabolism can damage the skin. Bacteria multiply by division, so-called mitosis, which under favourable conditions can be so rapid that the number of bacteria is doubled every twenty minutes. Under these conditions, bacteria can enter the urinary passages and cause infection. This occurs more easily in women, the urethra being shorter in women than in men.

In urine and faeces-incontinent individuals, i.e. those who do not have the ability to themselves control the time of discharge for urine and excrement, there is often the problem of urinary infections and discomforting odor. The risk of bacteria growth increases since they always wear a diaper which is in contact with the skin, preventing air circulation and increasing perspiration. The diaper is often wet and the urine in the diaper, which because of the closeness to the body is kept warm, is a conducive growth medium for bacteria.

Of the above-mentioned bacteria, the Proteus group can break down urea. All of the Proteus strains form during their metabolism the enzyme urease, which has the ability to rapidly break down urea into ammonia. Normal human urine contains 2% urea, which means that from one liter of urine, about 50 ml of concentrated 25% ammonia solution can be released.

The ammonia not only produces an unpleasant odor, but a high pH value as well. Contact with a wet diaper with a high pH value eventually causes skin damage, so-called diaper rash. Such skin damage in the form of rash is conducive to bacteria growth, which in turn leads to the formation of ammonia thus initiating a self-maintaining process which causes urinary infection and unpleasant odor.

These problems are quite common in geriatic care, where many patients are urine-incontinent and use diapers and towels. Many women also have similar problems during their menstrual period.

The purpose of the present invention is to eliminate these problems. It has been demonstrated that copper, even in very small amounts, has a strong lethal effect on all bacteria occurring in the perineal region on human beings. In vitro tests have shown that an amount of copper as little as 250 $\mu$g/ml soya bouillon effectively kills off within 24 hours an inoculate with more than $10^6$ bacteria per ml. Practical tests have also demonstrated that an amount of copper acetate as small as 0.25 g (dry weight) distributed over the surface of an incontinence diaper of the size $32 \times 65$ cm prevented bacteria growth and odor.

The invention relates to a germicidal absorbent body for collecting urine, faeces or blood and dimensioned to absorb a maximum amount of fluid, said absorbent body being characterized in that it contains a water-soluble copper salt, which does not hurt or irritate the skin, preferably concentrated to the surface of the absorbent body which first comes into contact with the urine, faeces or blood.

The absorbent body contains 150–700, preferably 200–500 and especially about 300 $\mu$g of copper per ml of the fluid volume which it is designed to absorb.

As the copper salt, any salt at all can be used which is soluble in the fluid which the absorbent body is to absorb, namely urine, blood or faeces. Examples of such water-soluble copper salts are copper borate, copper sulphate, copper chloride, copper formate, copper oxalate, copper acetate, copper tartrate, copper citrate and copper lactate. Preferably copper acetate is used, which has the advantage that acetate ions have an antibacterial effect as well.

The advantage of an absorbent body which according to the invention contains a water-soluble copper salt, is that the copper ions inhibit the growth of the bacteria occurring in the perineal region. This prevents the breaking-down of urea into odoriferous ammonia. If, however, ammonia should be formed, it can be formed into a complex by the copper ions into tetraamine cupric ion $[Cu(NH_3)_4]^{2+}$. This is especially important for urine-incontinent patients with urinary tract infections. Preferably copper acetate is used, since the acetate ions is protolyzed into acetic acid, which is a germicide.

What is meant by an absorbent body is an infant diaper, an incontinence diaper, a pad, a sanitary napkin or the like which is used for absorbing and collecting urine, faeces or blood. The absorbent material in such absorbent bodies usually consists of cellulose fibres or wadding. Such absorbent bodies can absorb 50 to 700 ml of fluid depending on whether it is the smallest type of infant diaper or a pad for urine incontinent persons.

The copper salt is introduced either directly in the cellulose fibres or wadding prior to fabrication of the absorbent body, or is dissolved in a solvent which is not harmful, preferably water, and is sprayed on one side of the finished absorbent body or on a component thereof. Said component then forms the side which first comes into contact with urine, blood or faeces.

A preferred absorbent body according to the invention consists of a sheet of fluffed cellulose fibre with a surface weight of 250–350 g/m$^2$. This fluffed sheet comprises the absorbent layer of the diaper and is dimensioned so that a finished diaper can absorb about 500 ml of urine. The fluffed sheet lies between two webs of soft paper which are stamped securely to the fluffed sheet in a stamping machine. The fluffed sheet with a double-sided soft paper surface is glued on one side to a thin plastic sheet which is impermeable to moisture and so much wider than the fluffed sheet that the edges of the plastic sheet can be folded over the two edges of the fluffed sheet and 2–3 cm in on the other side of the fluffed sheet. A thin, permeable net or non-woven material is fused or glued to these folded sheet edges. This net or non-woven material forms the side of the finished diaper which first comes into contact with urine, faeces or blood.

The fluffed sheet is 10-15 cm shorter than the total length of the finished diaper, so that each end of the diaper will only consist of a 5-7.5 cm long flap of plastic sheeting and the net or non-woven web fused or glued to this flap. This is done to prevent so-called edge leakage in the finished diaper. When using the present invention in such a diaper construction, it is most suitable to impregnate the uppermost soft paper sheet, i.e. that lying closest to the net or non-woven material, prior to stamping against the fluffed material, with an aqueous solution of a copper salt either by prefabrication in a separate apparatus or by a direct process "in line" in the diaper machine.

When working with copper acetate, the ratio between the concentration in the impregnating solution and the soft paper is adjusted so that the impregnated paper will contain 1.2-2.5 g of copper acetate per $m^2$, calculated as dry substance.

A hygienic napkin, for example, can be made in a similar manner. In principle, it is only the size and the absorbent material which vary somewhat.

Clinical tests have been performed with diapers of the type described above of a size $32 \times 65$ cm and dimensioned to absorb 300 ml of urine. The soft paper facing the top (against the net) was sprayed with an aqueous solution of copper acetate so that the soft paper received 0.25 g (dry weight) of copper acetate or 0.08 g of copper per diaper. This corresponds to 267 $\mu$g of copper per ml of the amount of urine which the diaper can absorb. A urine-incontinent woman with strongly smelling urine used a total of 112 of these diapers. The diapers were changed after an average of two hours. Of the diapers used 89% had no urine odor, 8% the odor or normal urine, and 4% smelled strongly. After the change to germicidal diapers, the urine smell disappeared from the room. When the patient again begun to use ordinary diapers, the unpleasant stink returned. No skin damage was noted.

The absorbent body treated with copper salt according to the invention prevents bacteria growth and breaking-down of urea into ammonia. Any ammonia formed is bonded and cannot be freed, so that the pH value does not rise and unpleasant odor does not occur. The diaper has practical advantages in that it impedes the occurrance of diaper rash, unpleasant odor and urinary infections.

What I claim is:

1. An odor-inhibiting and germicidal absorbent body for collecting urine or feces, said body comprising cellulose fibers or wadding, wherein the fibers or wadding at one surface of said body which, in use, first comes into contact with urine or feces are impregnated with an odor-inhibiting and germicidal solution consisting of an aqueous solution of a water-soluble copper salt selected from the group consisting of copper formate, copper oxalate, copper tartrate, copper citrate, copper lactate, copper sulfate, copper chloride, copper acetate and copper borate, said copper salt being concentrated in said fibers or wadding at said one surface such that there is present at least 150 $\mu$g copper per milliliter of the liquid volume which said absorbent body is dimensioned to absorb.

2. The odor-inhibiting and germicidal absorbent body of claim 1 wherein said copper salt is copper acetate present in an amount ranging from 1.2 to 2.5 g of copper acetate, calculated as dry substance, per $m^2$ of said surface which first comes into contact with urine or feces.

* * * * *